United States Patent [19]

Beijbom et al.

[11] Patent Number: 4,756,705
[45] Date of Patent: Jul. 12, 1988

[54] HEART-LUNG SYSTEM USING THE LUNG AS AN OXYGENATOR

[75] Inventors: Peter Beijbom; Staffan Grebius, both of Lund; Goran E. W. William-Olsson, Goteborg, all of Sweden

[73] Assignee: Gambro, AB, Sweden

[21] Appl. No.: 939,422

[22] Filed: Dec. 8, 1986

[30] Foreign Application Priority Data

Dec. 19, 1985 [SE] Sweden .................. 8506029

[51] Int. Cl.[4] .................................. A61M 37/00
[52] U.S. Cl. ........................................ 604/4; 55/178;
128/1 D; 128/399; 128/DIG. 3; 210/236;
210/258; 210/340; 210/436; 422/44
[58] Field of Search ............ 623/3; 128/1 D, DIG. 3,
128/399, 400; 604/4–6, 50, 66, 67; 55/178;
210/236, 340, 323.1, 436, 258, 252, 255;
422/44–48

[56] References Cited

U.S. PATENT DOCUMENTS

| | | | |
|---|---|---|---|
| 2,988,001 | 6/1961 | D'Arcey et al. | 128/DIG. 3 |
| 3,045,601 | 7/1962 | Rippingille | 128/DIG. 3 |
| 3,927,980 | 12/1975 | Leonard | 128/DIG. 3 |
| 3,993,067 | 11/1976 | Schachet et al. | 604/4 |
| 4,058,855 | 11/1977 | Runge | 128/DIG. 3 |
| 4,115,277 | 9/1978 | Swank | 210/436 |
| 4,261,951 | 4/1981 | Milev | 128/DIG. 3 |
| 4,642,089 | 2/1987 | Zupkas et al. | 55/178 |
| 4,662,355 | 5/1987 | Pieronne et al. | 128/1 D |
| 4,662,906 | 5/1987 | Matkovich et al. | 210/436 |
| 4,668,394 | 5/1987 | Badolato et al. | 604/5 |

OTHER PUBLICATIONS

Drake et al, "The Effect of Low Molecular Weight Dextron upon the Blood Flow during Extracorporeal Circulation", J. Thor. and Card. Surg., vol. 42, No. 6; 12161, pp. 735–741.

Primary Examiner—C. Fred Rosenbaum
Assistant Examiner—Mario Costantino
Attorney, Agent, or Firm—Lerner, David, Littenberg, Krumholz & Mentlik

[57] ABSTRACT

A cardiopulmonary system is disclosed which is intended for oxygenation of a patient's blood during heart surgery in which the patient's own lungs are used for such oxygenation. The cardiopulmonary system includes use of a blood reservoir which includes at least two chambers, one for venous blood collected from the patient's heart or a major vein and one for arterial blood, and include filters for filtering both the venous and arterial blood as they enter the respective chambers.

30 Claims, 3 Drawing Sheets

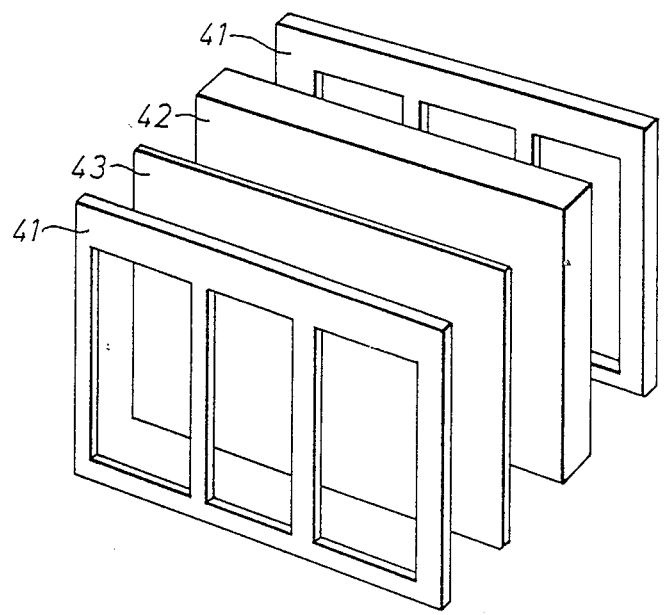

HEART-LUNG SYSTEM USING THE LUNG AS AN OXYGENATOR

FIELD OF THE INVENTION

The present invention relates to cardiopulmonary systems. More particularly, the present invention relates to cardiopulmonary systems intended for oxygenation of a patient's blood in conjunction with operations on or near the heart, and in particular in which the patient's lung or lungs are used for such oxygenation. Still more particularly, the present invention relates to such cardiopulmonary systems utilizing means to withdraw venous blood from the heart or from a major vein connected to the heart, and for conducting this blood through a chamber to one or both of the lungs for oxygenation, and then through a second chamber to the heart or another major vein connected to the heart.

BACKGROUND OF THE INVENTION

Systems of the above type which employ a patient's own lungs for oxygenation are described, for example, by M. H. Cass and D. N. Ross in an article entitled "The evolution of a by-pass technique using the lungs as an oxygenator," Guy' Hospital Reports 1959; 108:237-44.

However, since 1958 this system has essentially been forgotten, and different mechanical arrangements for the oxygenation of the blood have been used instead. In these systems the oxygen is either added directly to the blood in the form of bubbles, as described, for example, in U.S. Pat. No. 4,374,088, or it is supplied through a gas-permeable but water-tight membrane, as described, for example, in U.S. Pat. No. 3,612,281. More recently, however, there has been renewed interest in the older system as shown by Andre Bodnar and Donald Nixon Ross, for example, in their article "Bilateral Cardiac Bypass Without an Oxygenator for Coronary Surgery" in *Progress in Artificial Organs,* 1983.

One difficulty with this system, however, is that no appropriate equipment exists to carry it out, so that those who have attempted to make use of such a system have been compelled to create complicated systems comprising conventional cardiotomy reservoirs, blood pumps, filters and other control equipment. It is therefore an object of the present invention to make possible the use of the aforementioned system, but, with the assistance of very simple, yet nevertheless extremely reliable equipment.

SUMMARY OF THE INVENTION

In accordance with the present invention, these and other objects have now been realized by the invention of a cardiopulmonary system for the oxygenation of a patient's blood using the patient's own lungs for such oxygenation which includes blood collection means for collecting venous blood from the patient, arterial blood collection means for collecting arterial blood from the patient, a blood reservoir including a first venous blood chamber and a second arterial blood chamber, venous blood entry port means, arterial blood entry port means, venous blood filter means for filtering the venous blood adjacent the first venous blood chamber, arterial blood filter means for filtering the arterial blood adjacent the second arterial blood chamber, venous blood conduit means for conducting the venous blood from the venous blood collection means to the venous blood entry port means, arterial blood conduit means for conducting the arterial blood from the arterial blood collection means to the arterial blood entry port means, venous blood return means for returning the venous blood from the first venous blood chamber to the patient's lungs, and arterial blood return means for returning the arterial blood from the second arterial blood chamber to the patient's heart.

In accordance with another embodiment of the cardiopulmonary system of the present invention the blood reservoir includes a third drawn blood chamber for receiving blood from the patient, and drawn blood collection means for drawing blood from the patient and supplying it to the drawn blood chamber. In a preferred embodiment, the system includes third drawn blood filter means for filtering the drawn blood between the third drawn blood chamber and the first venous blood chamber, so that the filtered drawn blood can be admixed with the venous blood in the first venous blood chamber.

In accordance with another embodiment of the cardiopulmonary system of the present invention, the blood reservoir includes fluid connection means for providing fluid connection between the first venous blood chamber and the second arterial blood chamber. In a preferred embodiment, the blood reservoir is vertically disposed and includes an upper portion and a lower portion, and the fluid connection means includes venous blood port means and arterial blood port means located at the lower portion of the first venous blood chamber and the second arterial blood chamber, respectively, and a flexible conduit means for connecting the venous blood port means to the arterial blood port means.

In accordance with another embodiment of the cardiopulmonary system of the present invention, there is also provided venous blood heat exchange means for providing heat exchange with the venous blood in the first venous blood chamber, and arterial blood heat exchange for providing heat exchange with the arterial blood in the second arterial blood chamber. In a preferred embodiment, the venous blood heat exchange means and the arterial blood heat exchange means comprise spirally wound conduits contained within the first venous blood chamber and the second arterial blood chamber, respectively. Preferably, the venous blood heat exchange means and the arterial blood heat exchange means both include inlet and outlet means, each of which are provided in the upper portion of the blood reservoir. Most preferably, the lower portion of both the first venous blood chamber and the second arterial blood chamber have an arcuate shaped configuration, and the venous blood heat exchange means and the arterial blood heat exchange means are both located within the lower portions of the first venous blood chamber and the second arterial blood chamber, respectively. In a preferred embodiment, blood displacement means comprising a central cylindrical core about which the spirally wound conduits are provided.

In accordance with another embodiment of the cardiopulmonary system of the present invention, the blood reservoir includes a wall portion separating the first venous blood chamber from the second arterial blood chamber. In a preferred embodiment, the venous blood filter means and the arterial blood filter means comprise cassette means whereby both filter means are removably insertable within the blood reservoir. Preferably, the cassette means comprises frame means and filter members insertable within the frame means, and the filter members can comprise a first filter comprising a defoamer material and a second filter member comprising a fabric.

In accordance with another embodiment of the cardiopulmonary system of the present invention, the blood reservoir includes venous blood chamber atmosphere connection means permitting the release of gas within the first venous blood chamber to the atmosphere, as well as arterial blood chamber atmosphere connection means for permitting the release of gas within the second arterial blood chamber to the atmosphere. In a preferred embodiment, the venous blood chamber atmosphere connection means and the arterial blood chamber atmosphere connection means comprise sterile filter means.

In accordance with another embodiment of the cardiopulmonary system of the present invention, there is provided venous blood pump means and arterial blood pump means for pumping the blood through the venous blood conduit means and the arterial blood conduit means, respectively.

Therefore, in accordance with the present invention, a cardiopulmonary system is provided for oxygenation of a patient's blood in conjunction with an operation on or near the heart and in which the patient's own lung or lungs can be used for such oxygenation. The principal characteristic of this invention is that the apparatus includes a reservoir with at least two chambers, namely one for venous blood and one for arterial blood. In this manner, among other things, a regular supply of blood to the lungs is made possible, even if withdrawal of this venous blood from the patient were to be slightly irregular. At the same time use of such a two-chamber system renders it rather easy for the blood to be treated, such as being warmed up, on its way to and from the lungs.

Also in a preferred embodiment, the blood reservoir comprises a third chamber which is intended to serve essentially as a cardiotomy reservoir by receiving drawn out blood and the like which, after filtration, can preferably be mixed with the venous blood to be oxygenated jointly therewith.

The two chambers in the blood reservoir of this invention are preferably arranged so as to be in connection with each other as two communicating vessels. As a result, substantially the same level of fluid or blood is maintained in the two chambers and this facilitates the regular supply of blood to the lungs. In a preferred embodiment, this connection is achieved by a fully open, flexible external duct connected with its end to the chambers near to, or at, their lowest points. As a result, the actual design of the chambers can be rendered relatively simple, and at the same time the arrangement of filters and the like is not prevented thereby. Furthermore, if the duct is prepared from a flexible tube, it can easily be closed, if necessary, by the use of a spring clip or the like.

To enable the treated blood to be warmed up, the two chambers can be appropriately provided with their own heat exchangers. These are preferably formed simply by a single unbroken duct in the form of a horizontal helix-shaped spiral whose end connections are arranged above the maximum blood level within the reservoir. In this manner there is less danger of the heating medium leaking into the blood or vice versa. The heat exchanger is also preferably arranged at the bottom of the respective chambers, which are preferably in the shape of a semi-cylinder, and preferably the center core is filled with a cylinder for displacing the blood, which produces a very effective design only requiring a small amount of blood in order to function.

Even in the case where the blood is withdrawn substantially directly from the heart or from the lungs, the inlets to the two chambers are arranged so as to be separated from the respective main parts by a filter. This is even more important where the third chamber is used, since it is preferably adapted to be in communication with the chamber intended to receive venous blood by at least one filter. Filters are preferably built up in a conventional manner from a defoamer material, such as an anti-foam-treated polyurethane, together with a tricot fabric such as nylon or polyester or a deep filter. A preferable and simple design particularly from the point of view of manufacturing is obtained where the reservoir is built up in accordance with a cassette-type system which preferably includes a fixed wall between the two chambers and a number of loosely insertable filters arranged between the inlets and the respective chambers.

BRIEF DESCRIPTION OF THE DRAWINGS

The present invention will be described in greater detail in the following detailed description, with reference to the attached drawings in which:

FIG. 4 is an exploded, perspective view of a filter for inclusion in the reservoir shown in FIG. 2.

DETAILED DESCRIPTION

Figure 1:
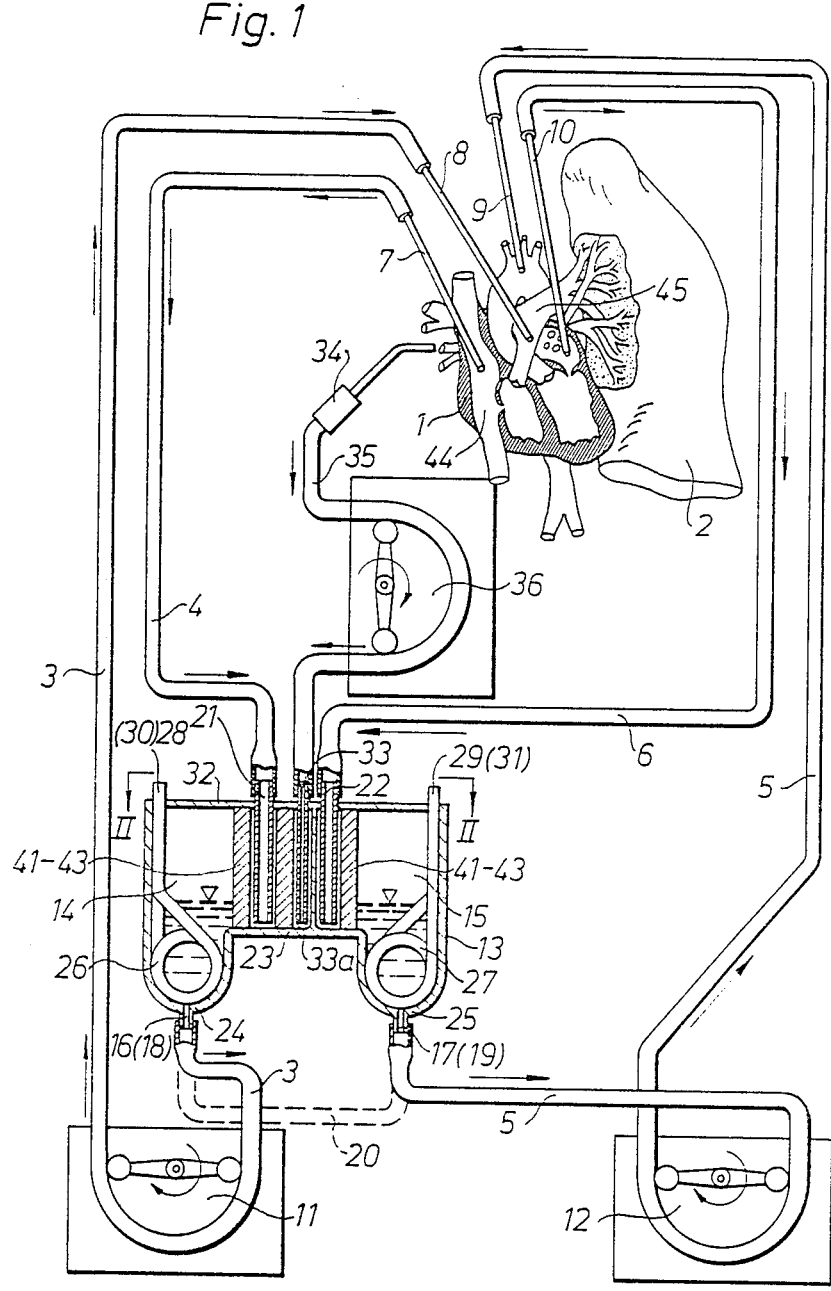
FIG. 1 is a schematic, partially sectional view of a cardiotomy system in accordance with the present invention.
Figure 3:
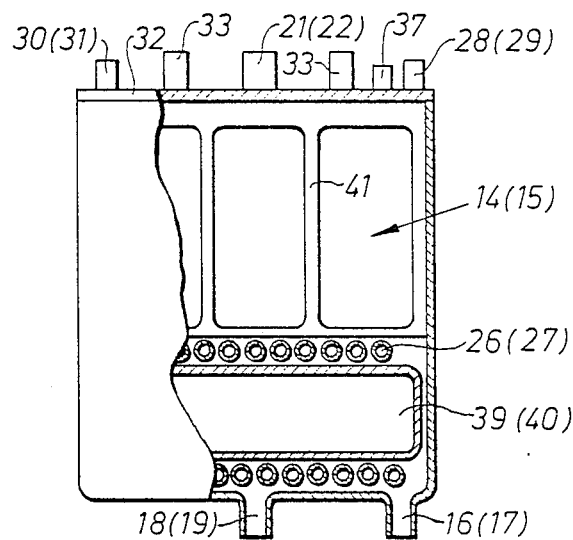
FIG. 3 is a side, partially sectional view of the reservoir shown in FIG. 2 taken along lines III—III thereof.

Referring next to the figures, in which like numerals refer to like portions thereof, FIG. 1 shows an essentially complete system in accordance with the present invention, and is intended to illustrate how this system can be coupled to a patient's heart 1 and lungs 2. This is accomplished by means of ducts 3, 4, 5 and 6 attached to catheters or cannulas 7, 8, 9 and 10, respectively. The flow in ducts 3 and 5 in this case is obtained with the assistance of pumps 11 and 12. The flow in ducts 4 and 6 is obtained by means of the blood's own pressure, possibly reinforced by the force of gravity, in that a reservoir 13, to which all of these ducts are connected, is maintained at a location which is lower than the patient. Reservoir 13 includes two chambers, 14 and 15, which are intended for venous and arterial blood, respectively. Ducts 3 and 5 lead away from two nipples 16 and 17, which are arranged at the lowest points of the respective chambers 14 and 15. As is shown in FIG. 3, two other nipples 18 and 19 are provided which, as is shown schematically in FIG. 1 by a broken line, are connected to each other through a duct 20, so that the chambers 14 and 15 can thereby form two communicating vessels having substantially the same liquid level. Ducts 3 and 5, on the one hand, and duct 20, on the other, are thus respectively situated in different planes in FIG. 1. Ducts 4 and 6 open into two inlet pipes 21 and 22, respectively, which in turn extend to openings near the base 23 of reservoir 13, which is preferably maintained at an elevated temperature.

Figure 2:
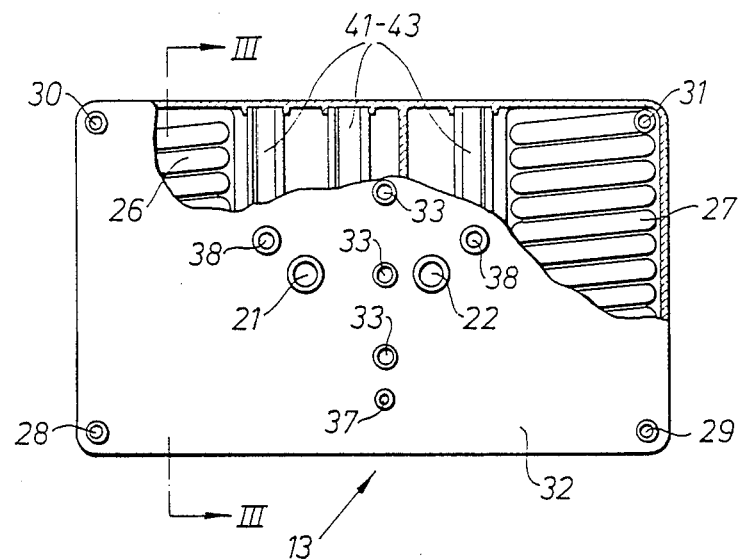
FIG. 2 is a top, elevational, partially sectional view of a reservoir used in accordance with the system shown in FIG. 1, taken along lines II—II thereof.

On either side of the intermediate base 23 chambers 14 and 15 are designed to have substantially semicylindrical chamber bases 24 and 25, respectively. These chamber bases are designed to be adapted to contain two heat exchangers 26 and 27, each of which is in the form of a horizontal helix-shaped spiral, whose inlets and outlets 28-31 are each arranged outside of their respective chambers, i.e., above the maximum blood level. These inlets and outlets can best be seen in FIG. 2, which shows the reservoir 13 from above, with its cover 32 partly removed. The inlet pipes 21 and 22 in this case are shown as two circles. Three additional inlet pipes 33 are intended to be connected to one or more suction devices 34, one of which is shown in FIG. 1. This connection is obtained through duct 35, with a suction pump 36 joined thereto. These inlet pipes 33 open out into a common chamber, which is designated 33a. A further inlet pipe 37, which is not shown in FIG. 1, is intended to be used for injection of a priming fluid, such as a physiologically acceptable salt solution, which fills up the system until it is replaced by the blood. Two further circles 38 shown in FIG. 2 represent two gas outlets, through which any gas set free within the reservoir can be discharged, which is preferably accomplished through two sterile filters.

In FIG. 3, it is shown how the respective heat exchangers, 26 and 27, surround cylindrical cores 39 and 40, respectively. FIG. 3 thus represents a section taken through one of the chambers 14 and 15. On the top in FIG. 3 there are shown the various connections 21, 22, 28-31, 33 and 37. Connections 21 and 22 are thus being arranged in a line with each other, while also concealing one of the connections 33. A frame, which is indicated by reference numeral 41, is shown in greater detail in FIG. 4 in a cassette-like pack. This pack may thus consist of two such frames 41, with a coarse filter 42 and a fine filter 43 arranged between them. The coarse filter 42 may, for example, consist of antifoam-treated polyurethane, while the fine filter 43 may, for example, comprise a tricot fabric, e.g., nylon or a polyester. Two such cassette-like filters are shown schematically in FIGS. 1 and 2 arranged between inlet pipes 21 and 22, respectively, and adjoining chambers 14 and 15, respectively. A third similar cassette-like filter may be arranged between inlet pipe 33 and inlet pipe 21, so as to achieve an extra filtration of blood from the suction device 34. In this filter, the tricot fabric is preferably replaced by so-called deep filters or screen-filters.

FIG. 1 is intended to illustrate application of the system in accordance with the present invention. This application should not require any further explanation for those versed in the art. In summary, it is carried out in a manner such that venous blood is withdrawn by means of catheter 7 from vena cava 44, and is caused to flow by its own pressure through duct 4, inlet pipe 21 and filter 41-43 into chamber 14. From there it is pumped with the assistance of pump 11 through duct 3 and catheter 8 to the pulmonary artery 45, and thus into the lung or lungs 2. From here the blood passes to the left atrium, from which it is withdrawn by means of catheter 10, and is conducted by means of duct 6 to inlet pipe 22, and by means of a second filter 41-43 to chamber 15. After suitable warming in this chamber, the blood is then passed by means of pump 12 through duct 5 and catheter 9 to the aorta or to one or more other major arteries.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim that:

1. A cardiopulmonary system for the oxygenation of a patient's blood in which said patient's lungs are employed for such oxygenation, comprising venous blood collection means for collecting venous blood from said patient, arterial blood collection means for collecting arterial blood from said patient, a blood reservoir comprising a housing, said housing including a first venous blood chamber, a second arterial blood chamber, venous blood entry port means in said first venous blood chamber, arterial blood entry port means in said second arterial blood chamber, venous blood filter means for filtering said venous blood adjacent said first venous blood chamber, arterial blood filter means for filtering said arterial blood adjacent said second arterial blood chamber, a third blood chamber for receiving blood from said patient, drawn blood collection means for drawing said blood from said patient and supplying said drawn blood to said third drawn blood chamber, drawn blood conduit means for conducting said drawn blood from said third drawn blood chamber to said first venous blood chamber, venous blood conduit means for conducting said venous blood from said venous blood collection means to said venous blood entry port means, arterial blood conduit means for conducting said arterial blood from said arterial blood collection means to said arterial blood entry port means, venous blood return means for returning said venous blood from said first venous blood chamber to said patient's lungs, and arterial blood return means for returning said arterial blood from said second arterial blood chamber to said patient's heart.

2. The cardiopulmonary system of claim 1, including third drawn blood filter means in said drawn blood conduit means for filtering said drawn blood between said third drawn blood chamber and said first venous blood chamber whereby said filtered drawn blood can be admixed with said venous blood in said first venous blood chamber.

3. The cardiopulmonary system of claim 1, including fluid connection means for providing fluid connection between said first venous blood chamber and said second arterial blood chamber.

4. The cardiopulmonary system of claim 3, wherein said blood reservoir is vertically disposed and includes an upper portion and a lower portion, wherein said fluid connection means includes venous blood port means and arterial blood port means located at said lower portion of said first venous blood chamber and said second arterial blood chamber, respectively, and flexible conduit means connecting said venous blood port means to said arterial blood port means.

5. The cardiopulmonary system of claim 1, including venous blood heat exchange means for providing heat exchange with said venous blood in said first venous blood chamber, and arterial blood heat exchange means for providing heat exchange with said arterial blood in said second arterial blood chamber.

6. The cardiopulmonary system of claim 5, wherein said venous blood heat exchange means and said arterial blood heat exchange means comprise spirally wound conduits contained within said first venous blood chamber and said second arterial blood chamber, respectively.

7. The cardiopulmonary system of claim 6, wherein said blood reservoir is vertically disposed and includes an upper portion and a lower portion, wherein said venous blood heat exchange means and said arterial blood heat exchange means each include inlet and outlet means, and wherein said inlet and outlet means are provided in said upper portion of said blood reservoir.

8. The cardiopulmonary system of claim 7, wherein said lower portion of said first venous blood chamber and said second arterial blood chamber have an arcuate shaped configuration, and wherein said venous blood heat exchange means and said arterial blood heat exchange means are located within said lower portions of said first venous blood chamber and said second arterial blood chamber, respectively.

9. The cardiopulmonary system of claim 8, including blood displacement means comprising a central cylindrical core about which said spirally wound conduits are wound.

10. The cardiopulmonary system of claim 1, wherein said blood reservoir includes a wall portion separating said first venous blood chamber from said second arterial blood chamber.

11. The cardiopulmonary system of claim 10, wherein said venous blood filter means and said arterial blood filter means comprise cassette means whereby said venous blood filter means and said arterial blood filter means are removably insertable within said blood reservoir.

12. The cardiopulmonary system of claim 11, wherein said cassette means comprises frame means and filter members insertable within said frame means.

13. The cardiopulmonary system of claim 12, wherein said filter members comprise a first filter member comprising a defoamer material and a second filter member comprising a fabric.

14. The cardiopulmonary system of claim 13, wherein said defoamer material comprises anti-foam-treated polyurethane, and wherein said fabric comprises tricot fabric selected from the group consisting of nylon and polyester fabric.

15. The cardiopulmonary system of claim 1, wherein said drawn blood filter means comprises cassette means which is removably insertable within said blood reservoir.

16. The cardiopulmonary system of claim 1, wherein said blood reservoir includes venous blood chamber atmosphere connection means for permitting the release of gas within said first venous blood chamber to the atmosphere, and arterial blood chamber atmosphere connection means for permitting the release of gas within said second arterial blood chamber to the atmosphere.

17. The cardiopulmonary system of claim 16, wherein said venous blood chamber atmosphere connection means and said arterial blood chamber atmosphere connection means comprise sterile filter means.

18. The cardiopulmonary system of claim 1, including venous blood pump means and arterial blood pump means for pumping said blood through said venous blood conduit means and said arterial blood conduit means, respectively.

19. A cardiopulmonary system for the oxygenation of a patient's blood in which said patient's lungs are employed for such oxygenation, comprising venous blood collection means for collecting venous blood from said patient, arterial blood collection means for collecting arterial blood from said patient, a blood reservoir comprising a housing, said housing including a first venous blood chamber, a second arterial blood chamber, venous blood entry port means in said first venous blood chamber, arterial blood entry port means in said second arterial blood chamber, venous blood filter means for filtering said venous blood adjacent said first venous blood chamber, arterial blood filter means for filtering said arterial blood adjacent said second arterial blood chamber, venous blood heat exchange means for providing heat exchange with said venous blood in said first venous blood chamber, arterial blood heat exchange means for providing heat exchange with said arterial blood in said second arterial blood chamber, venous blood conduit means for conducting said venous blood from said venous blood collection means to said venous blood entry port means, arterial blood conduit means for conducting said arterial blood from said arterial blood collection means to said arterial blood entry port means, venous blood return means for returning said venous blood from said first venous blood chamber to said patient's lungs, and arterial blood return means for returning said arterial blood from said second arterial blood chamber to said patient's heart.

20. The cardiopulmonary system of claim 19 wherein said venous blood heat exchange means and said arterial blood heat exchange means comprise spirally wound conduits contained within said first venous blood chamber and said second arterial blood chamber, respectively.

21. The cardiopulmonary system of claim 20 wherein said blood reservoir is vertically disposed and includes an upper portion and a lower portion, wherein said venous blood heat exchange means and said arterial blood heat exchange means each include inlet and outlet means, and wherein said inlet and outlet means are provided in said upper portion of said blood reservoir.

22. The cardiopulmonary system of claim 21 wherein said lower portion of said first venous blood chamber and said second arterial blood chamber have an arcuate shaped configuration, and wherein said venous blood heat exchange means and said arterial blood heat exchange means are located within said lower portions of said first venous blood chamber and said second arterial blood chamber, respectively.

23. The cardiopulmonary system of claim 22, including blood displacement means comprising a central cylindrical core about which said spirally wound conduits are wound.

24. The cardiopulmonary system of claim 19 wherein said housing further includes a third drawn blood chamber for receiving blood from said patient, drawn blood collection means for withdrawing said blood from said patient and supplying said drawn blood to said third drawn blood chamber, and drawn blood conduit means for conducting said drawn blood from said third drawn blood chamber to said first venous blood chamber.

25. The cardiopulmonary system of claim 24 including third drawn blood filter means in said drawn blood conduit means for filtering said drawn blood between said third drawn blood chamber and said first venous blood chamber whereby said filtered drawn blood can be mixed with said venous blood in said first venous blood chamber.

26. The cardiopulmonary system of claim 19 wherein said housing further includes a wall portion separating said first venous blood chamber from said second arterial blood chamber.

27. The cardiopulmonary system of claim 26 wherein said venous blood filter means and said arterial blood filter means comprise cassette means whereby said venous blood filter means and said arterial blood filter means are movably insertable within said blood reservoir.

28. The cardiopulmonary system of claim 27 wherein said cassette means comprises frame means and filter members insertable within said frame means.

29. The cardiopulmonary system of claim 28 wherein said filter members comprise a first filter member comprising a defoamer material and a second filter member comprising a fabric.

30. The cardiopulmonary system of claim 29 wherein said defoamer material comprises anti-foam treated polyurethane and wherein said fabric comprises tricot fabric selected from the group consisting of nylon and polyester fabric.

* * * * *